US011318289B2

(12) United States Patent
Walish et al.

(10) Patent No.: US 11,318,289 B2
(45) Date of Patent: May 3, 2022

(54) URETERAL STENT

(71) Applicant: Gyrus ACMI, Inc., Southborough, MA (US)

(72) Inventors: Judy L. Walish, West Roxbury, MA (US); Hui Tang, Acton, MA (US); Thomas J. Holman, Princeton, MN (US)

(73) Assignee: Gyrus Acmi, Inc., Westborough, MA (US)

( * ) Notice: Subject to any disclaimer, the term of this patent is extended or adjusted under 35 U.S.C. 154(b) by 125 days.

(21) Appl. No.: 15/941,598

(22) Filed: Mar. 30, 2018

(65) Prior Publication Data
US 2019/0298978 A1 Oct. 3, 2019

(51) Int. Cl.
*A61F 2/04* (2013.01)
*A61M 27/00* (2006.01)
*A61L 31/04* (2006.01)

(52) U.S. Cl.
CPC ............. *A61M 27/008* (2013.01); *A61F 2/04* (2013.01); *A61L 31/042* (2013.01); *A61F 2002/048* (2013.01); *A61L 2430/22* (2013.01); *A61M 2210/1085* (2013.01)

(58) Field of Classification Search
CPC ......... A61M 27/008; A61M 2210/1085; A61F 2/82; A61F 2/04–042; A61F 2002/041–048; A61F 5/0076; A61L 2430/22
See application file for complete search history.

(56) References Cited

U.S. PATENT DOCUMENTS

| | | | | |
|---|---|---|---|---|
| 4,553,959 A * | 11/1985 | Hickey | ................. | A61M 25/10 604/103.09 |
| 5,531,718 A * | 7/1996 | Sachse | ...................... | A61F 2/94 604/530 |
| 6,582,472 B2 * | 6/2003 | Hart | .......................... | A61F 2/04 604/8 |
| 2003/0195456 A1 | 10/2003 | Robertson | | |
| 2003/0199986 A1 | 10/2003 | Mcweeney et al. | | |
| 2004/0059279 A1 * | 3/2004 | McWeeney | ............... | A61F 2/94 604/8 |

(Continued)

FOREIGN PATENT DOCUMENTS

CN 110327140 A 10/2019
EP 3546017 A1 10/2019

(Continued)

OTHER PUBLICATIONS

"European Application Serial No. 19164772.6, Extended European Search Report dated Sep. 2, 2019", 6 pgs.

(Continued)

*Primary Examiner* — Brian A Dukert
*Assistant Examiner* — Rebecca Lynee Zimmerman
(74) *Attorney, Agent, or Firm* — Schwegman Lundberg & Woessner, P.A.

(57) ABSTRACT

A ureteral stent is provided. The stent may include a first section having a first wall defining a first luminal section. The stent may further include a second section having a second wall defining a second luminal section. The second section can be enabled to substantially close at times external pressure is applied to the stent.

11 Claims, 11 Drawing Sheets

(56) References Cited

U.S. PATENT DOCUMENTS

| | | | |
|---|---|---|---|
| 2004/0143209 A1* | 7/2004 | Liu ..................... | A61M 27/008 |
| | | | 604/8 |
| 2006/0259151 A1 | 11/2006 | Ward | |
| 2008/0086214 A1* | 4/2008 | Hardin ..................... | A61F 2/04 |
| | | | 623/23.7 |
| 2011/0196507 A1* | 8/2011 | St. Pierre .......... | A61M 25/0009 |
| | | | 623/23.66 |
| 2014/0052272 A1* | 2/2014 | Amos, Jr. ............ | A61M 27/008 |
| | | | 623/23.69 |
| 2014/0151065 A1* | 6/2014 | Stephenson ............ | E21B 34/063 |
| | | | 166/374 |
| 2014/0188247 A1* | 7/2014 | Gandhi ..................... | A61F 2/04 |
| | | | 623/23.66 |
| 2016/0185482 A1 | 6/2016 | Youell et al. | |

FOREIGN PATENT DOCUMENTS

| | | |
|---|---|---|
| WO | WO-0191668 A1 | 12/2001 |
| WO | WO-02089893 A1 | 11/2002 |

OTHER PUBLICATIONS

"European Application Serial No. 19164772.6, Response filed Mar. 30, 2020 to Extended European Search Report dated Sep. 2, 2019", 5 pgs.

"European Application Serial No. 21175131.8, Extended European Search Report dated Nov. 24, 2021", 7 pgs.

* cited by examiner

URETERAL STENT

FIELD

The present disclosure relates to a medical device, and more particularly to a ureteral stent.

BACKGROUND

A ureteral stent may be placed inside a patient to assist in urinary drainage from a kidney to a bladder. For example, after some ureteral stone procedures, pieces or fragments of the stone or tumor can drop down into the ureter which may disrupt or block the flow of urine from the kidney to the bladder. The ureteral stent may function to allow the ureter to dilate and provide for the stone or stone fragments to pass and allow urine to flow from the kidney to the bladder.

A ureteral stent generally comprises a tubular member that terminates at two opposing ends. The tubular member allows the urine to flow through. However, current stents can cause significant discomfort to patients during voiding.

SUMMARY

It may therefore be desirable to improve the current state of the art by providing a ureteral stent that can be placed inside a patient to provide a passageway for urinary drainage from a kidney to a bladder, while minimizing discomfort to the patient.

The present disclosure provides a ureteral stent which significantly minimizes discomfort to a patient during voiding. A possible cause of discomfort can occur during drainage of urine through a stent. When the bladder muscles push urine out, some part of the urine can flow back to the kidney through the stent. Back flow of the urine to the kidney can be the possible cause of flank pain.

According to certain embodiments, a stent is provided. The stent may include a first section having a first wall defining a first luminal section and a second section having a second wall defining a second luminal section. The second section may be enabled to substantially close at times external pressure is applied to the stent.

BRIEF DESCRIPTION OF THE DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every figure. The drawings are not necessarily to scale, emphasis instead being placed upon illustrating embodiments, principles, and concepts. Thus, features and advantages of the present disclosure will become more apparent from the following detailed description of exemplary embodiments thereof taken in conjunction with the accompanying drawings.

DETAILED DESCRIPTION

These teachings are directed to a stent. The stent may be a medical stent. The stent may be any stent, such as a ureteral stent. The ureteral stent may function to assist in fluid or urinary drainage from the kidney to the bladder in patients. For example, after some ureteral stone or tumor medical procedures, pieces or fragments of the stone or tumor can drop down into the ureter, which may disrupt or block the flow of urine from the kidney to the bladder. The ureteral stent may function to allow the ureter to dilate, which may provide for the stone or stone fragments to pass and allow fluid or urine to flow from the kidney to the bladder.

Figure 1:
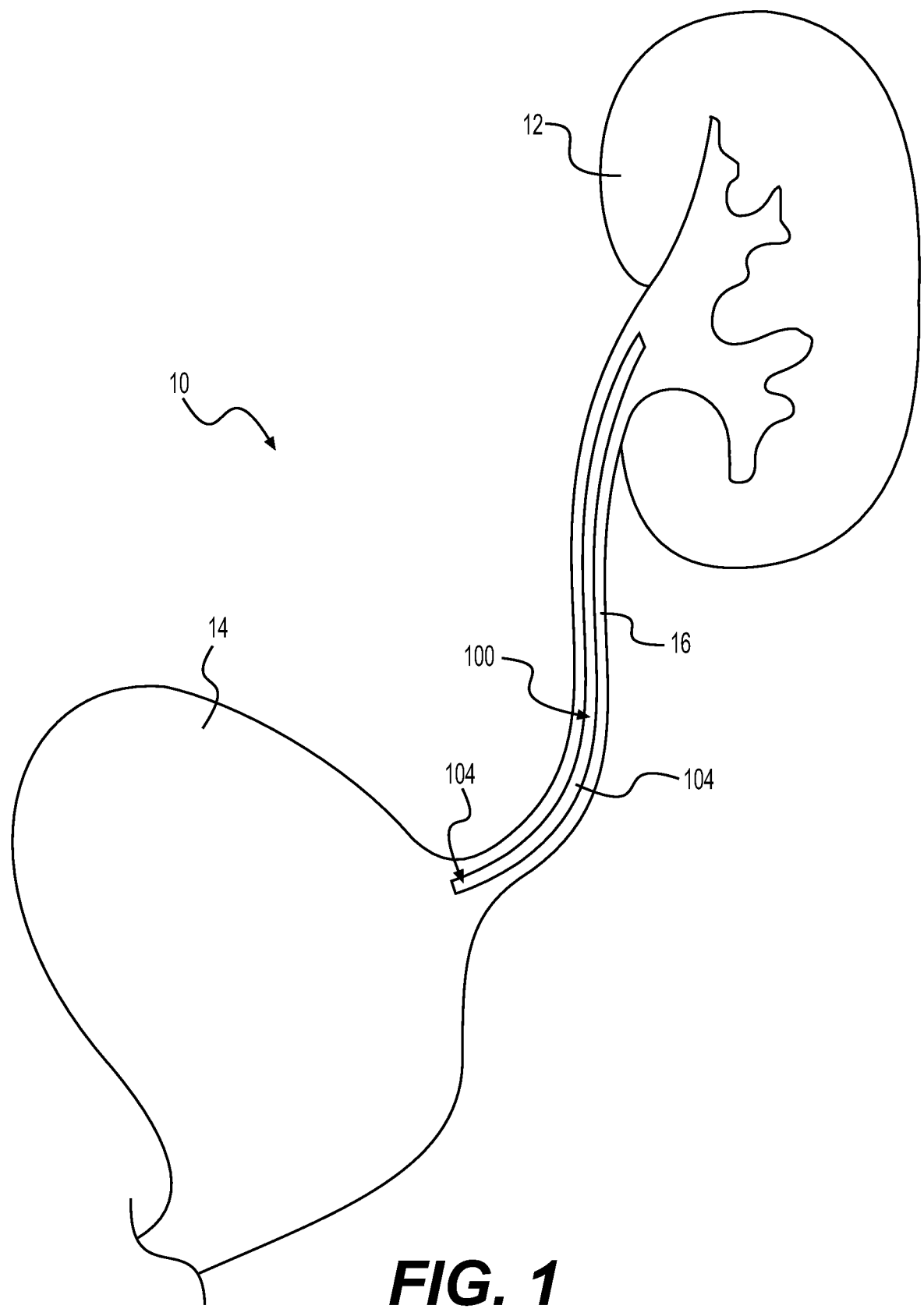
FIG. 1 is an illustration of a ureteral stent according to certain embodiment of the present invention placed in a kidney, a ureter, and a bladder of a patient.

FIG. 1 illustrates a stent 100 according to an example embodiment of the present invention. The stent 100 is illustrated inside a urinary tract 10 of a patient. One end of the stent 100 is placed inside a kidney 12 of the patient, and the opposing end is placed inside a bladder 14 of the patient.

Figure 2A:
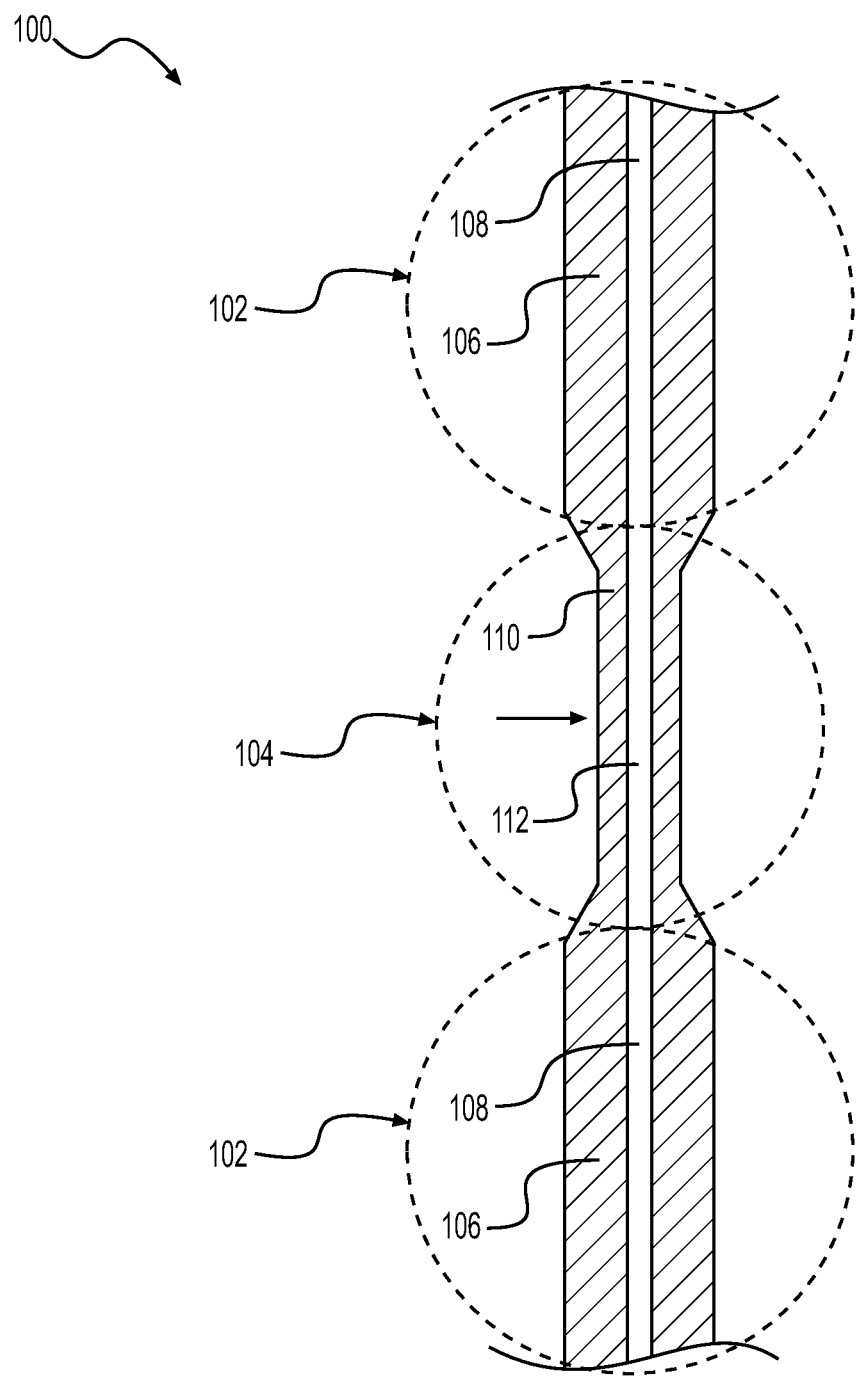
FIGS. 2A-2B are sectional views of a portion of a stent, according to certain embodiments.

FIG. 2A illustrates a portion of a stent 100 according to certain embodiments. The stent 100 may comprise a first section 102 and a second section 104. The first section 102 may include a first wall 106 defining a first luminal section 108. The second section 104 may include a second wall 110 defining a second luminal section 112. The first and the second sections may be placed in the urinary tract 10 of the patient. The second section 104 can be placed in the bladder 14. In some embodiments, the second section 104 can be placed in the ureter section 16. The first and the second sections generally may be hollow members that include an opening or lumen that extends from one retaining end to another end.

The first luminal section 108 and the second luminal section 112 may function to allow a wire to pass through the tubular member to assist with inserting and removing the stent in the patient. The first luminal section 108 and the second luminal section 112 may have a suitable size or diameter to be able to insert and remove the wire. The diameter of the first luminal section 108 and the second luminal section 112 may be on the order of about 0.040 inches to about 0.045 inches; however, larger and smaller sizes may be used depending on the specific use for the stent. Once inserted into the patient, the first luminal section 108 and the second luminal section 112 may also function to allow urine or other fluids to pass from the kidney 12 to the bladder 14.

The first wall 106 and the second wall 110 may have any suitable thicknesses. The thickness of the first wall 106 generally may be constant. In some embodiments, the thickness of the first wall 106 may vary through the stent. The thickness of the second wall 110 may vary or change along its length between larger and smaller cross sections, or different shapes. In some embodiments, the thickness of the second wall 110 is less than the first wall 106.

In some embodiments, the thickness of the first wall 106 or the second wall 110 could be on the order from about 0.1 mm to about 1.8 mm. In some configurations, it may be preferable for the diameter of the first wall and/or the second wall to be less than to 2.3 mm. The size of the second section 104 and/or first section 102 may have a French size (F) on the order from about 1 F to about 16 F; however, larger or smaller French sizes may be considered depending on the specific application of the stent.

The length of the stent 100 may be on the order of about 50 mm to about 350 mm; however, longer or shorter lengths may be considered depending on the specific application of the stent.

Figure 2B:
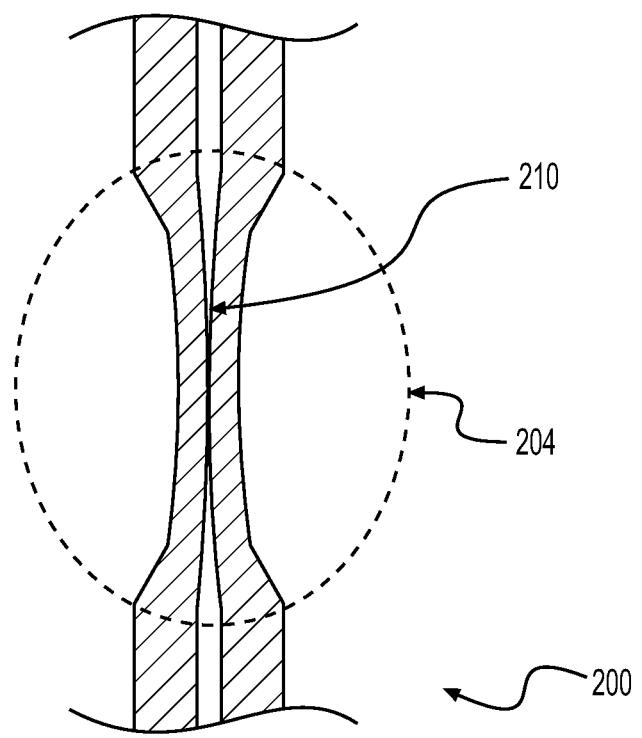

FIG. 2B illustrates a stent 200, such as the stent 100 of FIG. 2A, at times external pressure is applied to the stent 200 according to certain embodiments. The external pressure can be a pressure of peristalsis of the ureter contraction, fluidic pressure around the stent in the ureter, or the fluidic pressure in the bladder. As FIG. 2B illustrates, the second section 204 is substantially closed due to the external pressure, while the first section 102 is open to pass fluid. In one embodiment, the second section 104 of the stent 100 is enabled to substantially close at times external pressure is applied to the stent 100. The second section 104 of the stent 100 can be closed under external pressure. The closing may occur due to the difference in material properties, e.g., various geometries, non-uniformity of material, dimensions, etc. By closing the second section 104 of the stent 100, the fluid, e.g., urine, cannot go back toward the kidney 12 through the stent 100. The back flow of the urine and/or fluid to the kidney may cause significant discomfort to the patient. Accordingly, the second section 104 may act as a one-way valve.

In some embodiments, the second wall 110 of the second section 104/204 can be made of a material with a lower durometer than the first wall 106 of the first section 102; therefore, assisting in allowing the second section 104 to close under pressure. In some embodiments, the second section 104/204 may have a second wall 110/210 having lesser thickness than the first wall 106.

The first luminal section 108 and the second luminal section 112 may have any cross-sectional size or shape. For example, the first luminal section and/or the second luminal section may be circular, round, spherical, rectangular, square, or a combination thereof in cross-section.

Figure 3B:
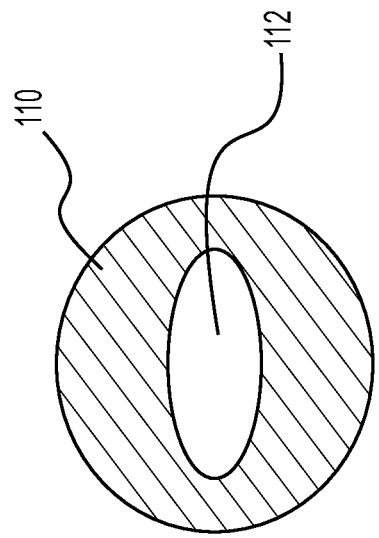
FIGS. 3A-3B are cross sectional views of a portion of a stent, according to certain embodiments.
Figure 3A:
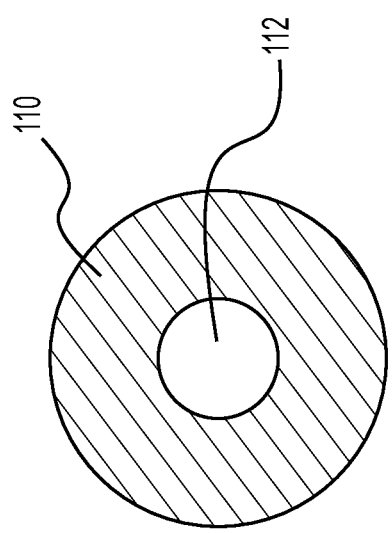

FIGS. 3A and 3B illustrate cross sectional views of a portion of a stent, such as the stent 100 illustrated in FIG. 2A, according to certain embodiments. FIG. 3A illustrates the stent 100 having a circular cross section. FIG. 3B illustrates the stent 100 having oval or semi oval cross section. As shown in FIG. 3B, the stent 100 can have a round outer surface, i.e., cylindrical shape, and an oval shape luminal section 112.

The first section 102 and the second section 104 may have any suitable cross section. For example, the cross section of the first section 102 and the second section 104 may be generally round or circular, hexagonal, elliptical, oval, or any geometry shape. The cross section generally may be consistent between the two opposing ends (i.e., generally round along an entire length of the stent 100); or the cross section of the first section 102 and the second section 104 generally may be inconsistent along an entire length thereof (i.e., some portions of the stent may have a generally round cross section and then other parts may have an oval or flat cross section).

In some embodiments, the stent 100 is adapted to minimize tissue irritation by way of reducing the contact areas between the stent 100 and tissue, such as the ureter 16, or the bladder 14. In some embodiments, the stent 100 is adapted to minimize tissue irritation by way of increasing flexibility using material with various durometer in the stent 100.

Figure 4:
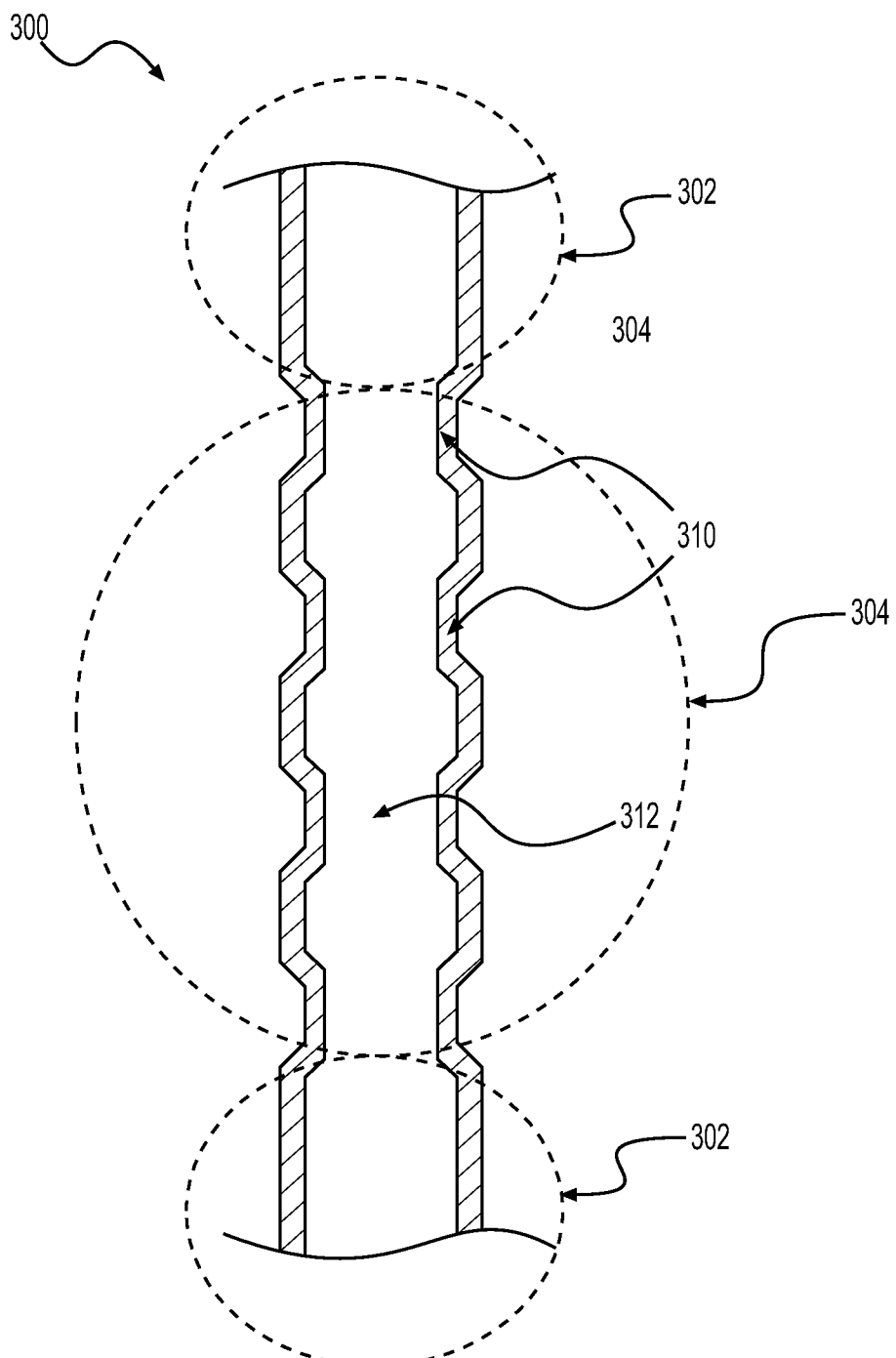
FIG. 4 is a sectional view of a portion of a stent, according to certain embodiments.

FIG. 4 illustrates a stent 300 having a first section 302 and a second section 304. The second section 304 may have a plurality of sections having respective walls 310 defining luminal sections 312 enabled to substantially close at times external pressure is applied to the stent 300.

In some embodiments, the stent may be made of one or more materials. The one or more materials of the stent may resist tissue adherence and encrustation. The one or more materials may be soft or flexible such that the stent and/or retaining ends may conform to a lumen or passageway of a patient into which the stent is inserted. The one or more materials may be strong enough such that the stent and/or retaining ends provide support for the body passageway or maintain the body passageway at a certain diameter.

According to certain embodiments, the one or more materials of the stent, the first section, and the second section may comprise Chitosan, silicone, polyurethane, polyethylene blend, polytetrafluoroethylene (PTFE), thermoplastic polyurethane (TPU), polyolefin elastomer (POE), Ethylene-vinyl acetate (EVA), Polystyrene-butadiene-styrene (SBS), silicone rubber, Nylon, Polyethylene or polythene (PE), polypropylene (PP), thermoplastics, C-Flex™, Percuflex™, Tecoflex™; Pebax®, stainless steel, metal, a metal alloy, Nitinol materials, nickel, titanium alloy super alloy, chromium cobalt, or a combination thereof. The material may comprise a shape memory material. The first section and/or the second section may comprise two or more materials (i.e., dual durometer or multi-durometer) that transition from a firm material at the tubular member to a soft or flexible material at the retaining ends. The material may be a swelling polymer that is adapted to expand when in contact with a fluid or when subjected to an increase in temperature, such as for example when the stent is located inside the patient.

The stent may be inserted or implanted inside a patient according to a method. The method may include a step of inserting a guide wire into the patient and advancing the guidewire into the bladder and then into the kidney. The method then includes a step of loading or feeding the stent onto the guidewire. The method includes a step of pushing or feeding the stent along the guidewire into the patient. The stent then may remain inside the patient to allow the ureter to dilate, which may provide for the stone or stone fragments to pass and allow urine to flow from the kidney to the bladder. The stent may remain permanently in the patient. The stent may be made of a biodegradable material where the stent dissolves or degrades inside the patient over time. The stent may be removed from the patient by inserting another guidewire into the patient and through the stent.

FIGS. 5-10 are graphs plotting Pressure (Pcr) applied to the stent vs. thickness of a section of stent (t); according to various example embodiment combinations of stent French size and materials. FIGS. 5-10 illustrate computational modeling data for stents having a second section with three different lengths that made from materials with various modulus of elasticity, which closes at various wall thicknesses. That is, the second section of the stent can close at times the external pressure of about 40-60 cm H2O is applied to the stent.

Flugge's formulation (EQ. 1 below) for the linear theory of orthotropic cylindrical shell was adopted to calculate instability of the stent 100 under external pressure. The external pressure may be fluid passing through or around the stent 100, movement of the patient, etc.

$$P_{cr} = [2\pi E t^2 (t/R)^{1/2} / [3(6)^{1/2} (1-\mu^2)^{2/3} RL]] * 10197.2 \quad \text{EQ. 1:}$$

In EQ. 1 above, R=radius of the stent 100 (mm); L=length of stent 100 (mm); t=thickness of stent 100 (mm); Pcr=critical pressure (cmH2O, 1 MPa=10197.2 cmH2O); E=modulus of elasticity (MPa); and μ=Poisson's ratio (μ=0.5 was selected).

A pressure in the renal artery during initial perfusion or passage of fluid through in the kidneys is on the order of about 40-60 cm H2O.

Figure 5:
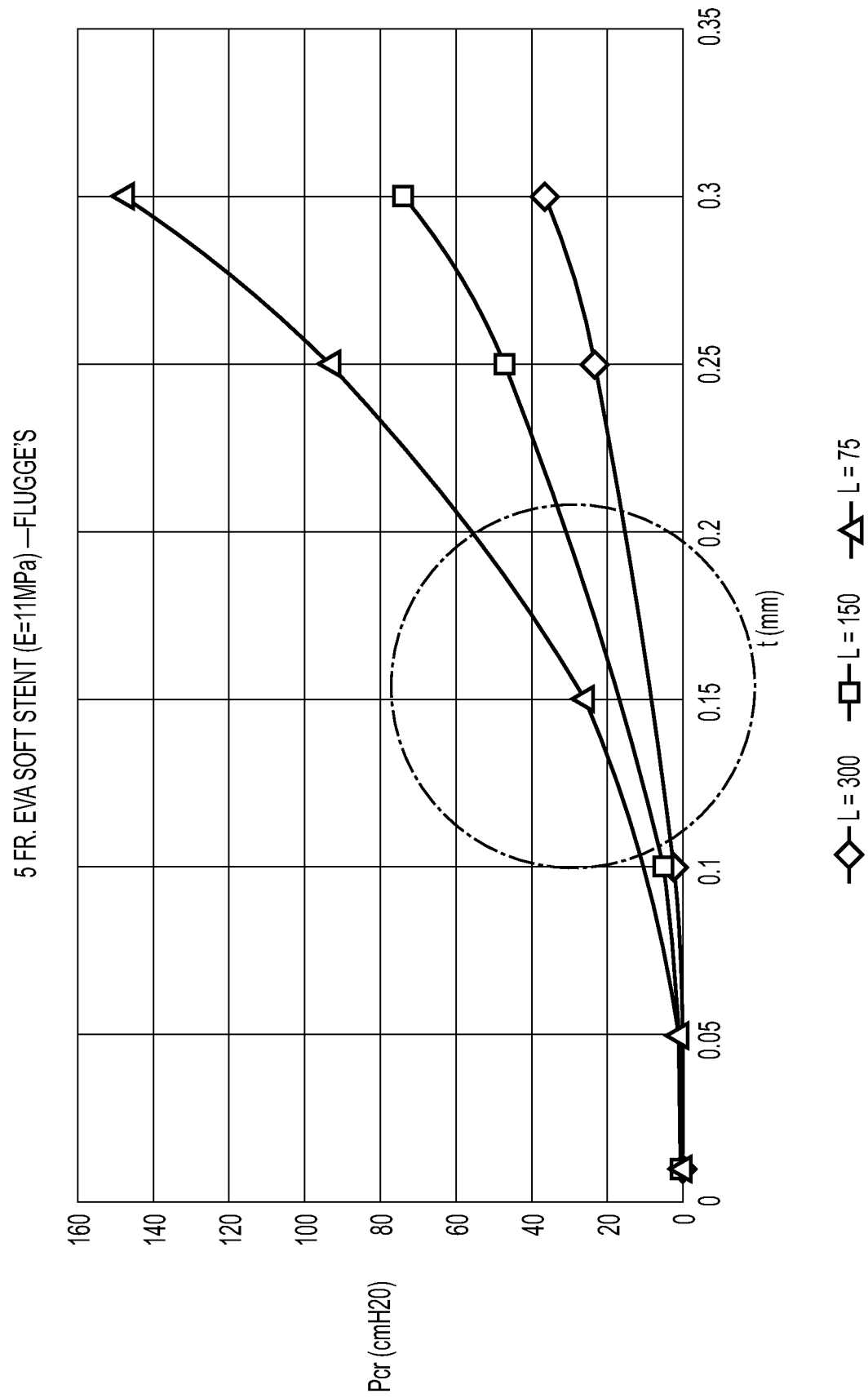
FIGS. 5-10 are graphs plotting Pressure (Pcr) applied to the stent vs. thickness of a section of stent (t); according to various example embodiment combinations of stent French size and materials.

Referring specifically to FIG. 5, three different stents having a 5 Fr. size made of EVA material having a modulus of elasticity of 11 MPa were tested.

As illustrated in FIG. 5, a first stent having a second section with a length of 300 mm does not fell within the external pressure range of 40 cm H2O to 60 cm H2O. A second stent having a second section with a length of 150 mm fell within the pressure range of 40 cm H2O to 60 cm H2O at a wall thickness about 0.23 mm to 0.27 mm. A third stent having a second section with a length of 75 mm fell within the pressure range of 40 cm H2O to 60 cm H2O at a wall thickness about 0.17 mm to 0.2 mm.

Figure 6:
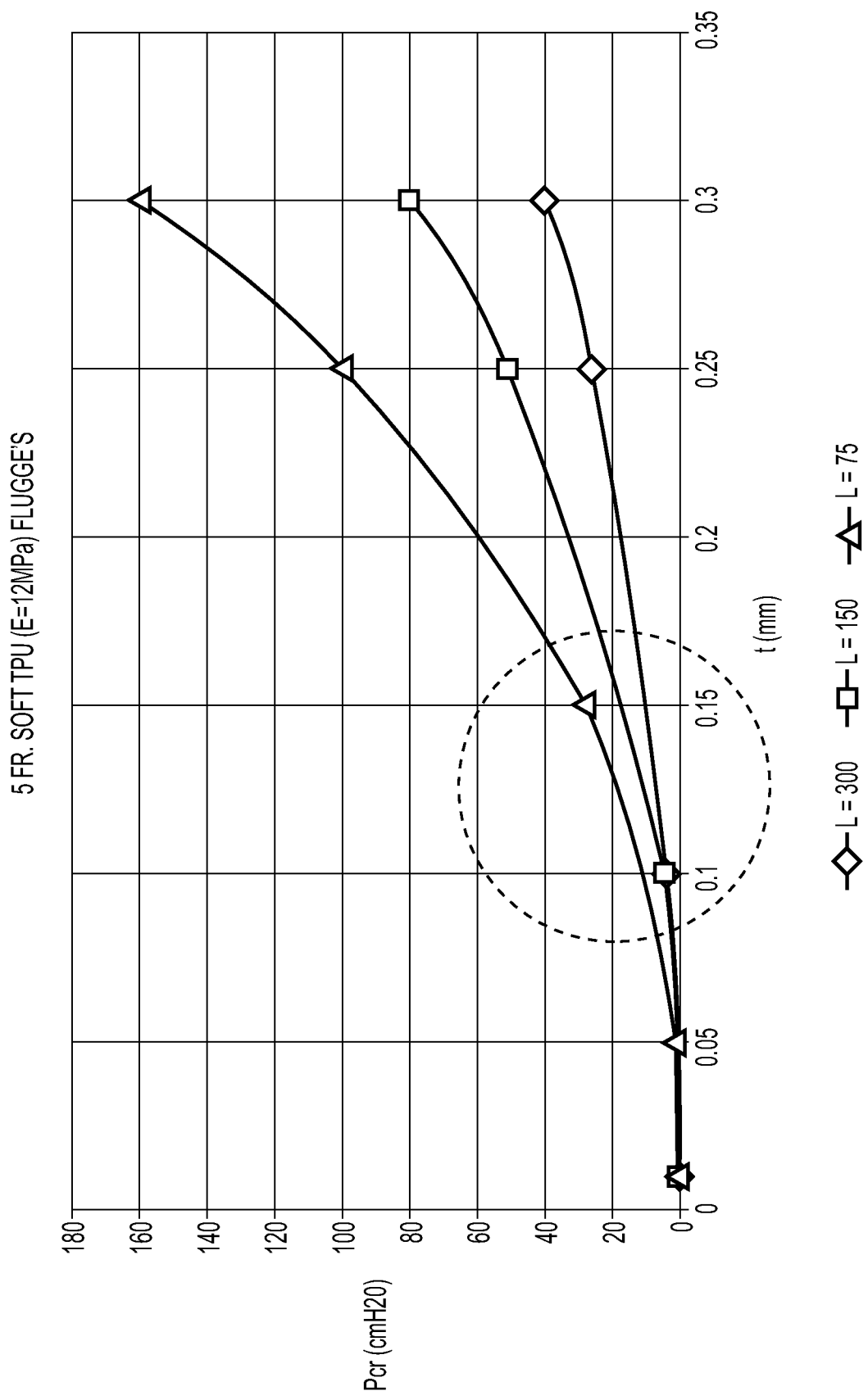

Referring specifically to FIG. 6, three different stents having a 5 Fr. size made of TPU material having a modulus of elasticity of 12 MPa were tested.

As illustrated in FIG. 6, a first stent having a second section with a length of 300 mm does not fell within the external pressure range of 40 cm H2O to 60 cm H2O. A second stent having a second section with a length of 150 mm fell within the pressure range of 40 cm H2O to 60 cm H2O at a wall thickness about 0.22 mm to 0.26 mm. A third stent having a second section with a length of 75 mm fell within the pressure range of 40 cm H2O to 60 cm H2O at a wall thickness about 0.17 mm to 0.2 mm.

Figure 7:
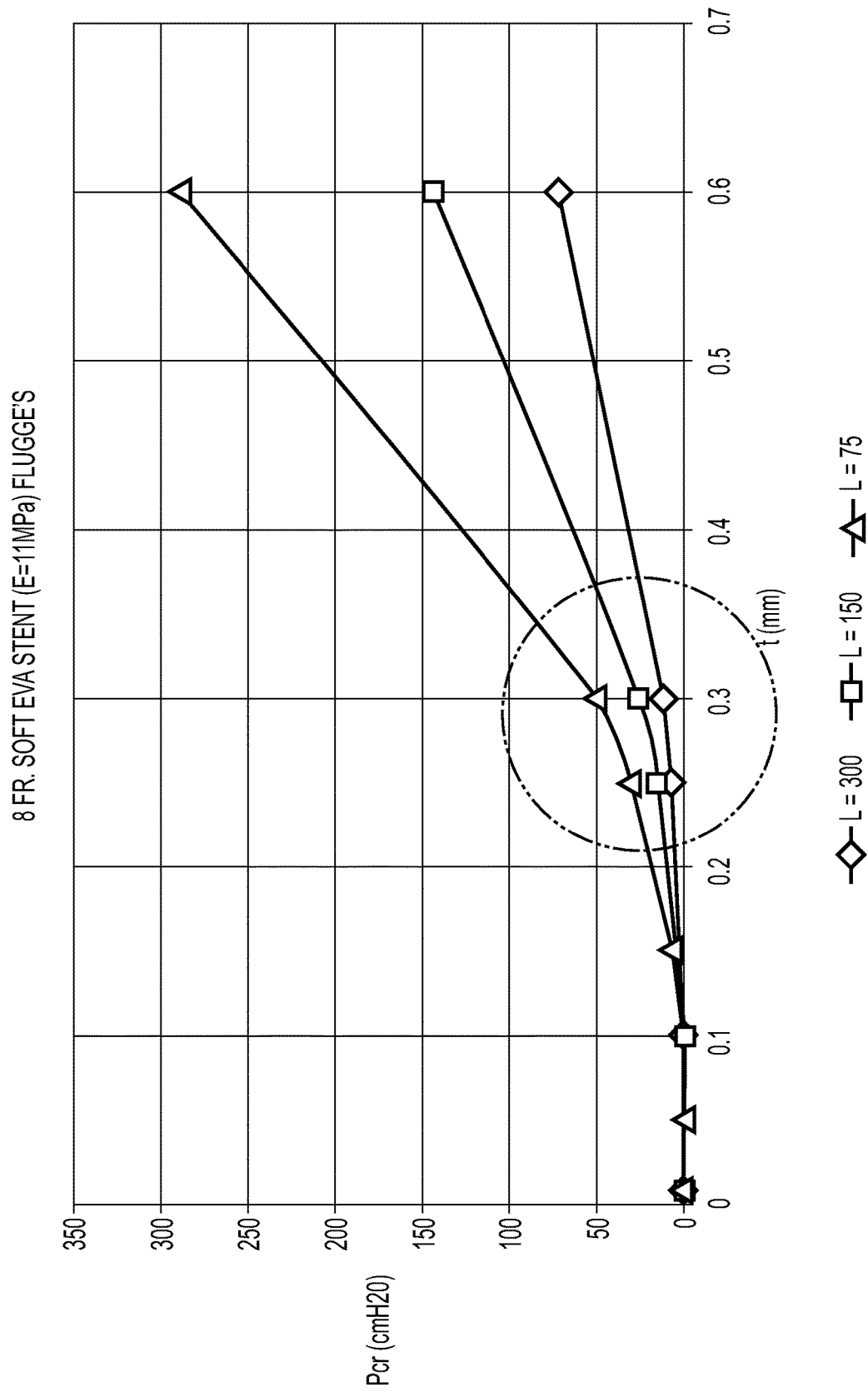

Referring specifically to FIG. 7, three different stents having a 8 Fr. size made of EVA material having a modulus of elasticity of 11 MPa were tested.

As illustrated in FIG. 7, a first stent having a second section with a length of 300 mm fell within the external pressure range of 40 cm H2O to 60 cm H2O at a wall thickness of about 0.47 mm to 0.51 mm. A second stent having a second section with a length of 150 mm fell within the pressure range of 40 cm H2O to 60 cm H2O at a wall thickness about 0.34 mm to 0.38 mm. A third stent having a second section with a length of 75 mm fell within the pressure range of 40 cm H2O to 60 cm H2O at a wall thickness about 0.25 mm to 0.3 mm.

Figure 8:
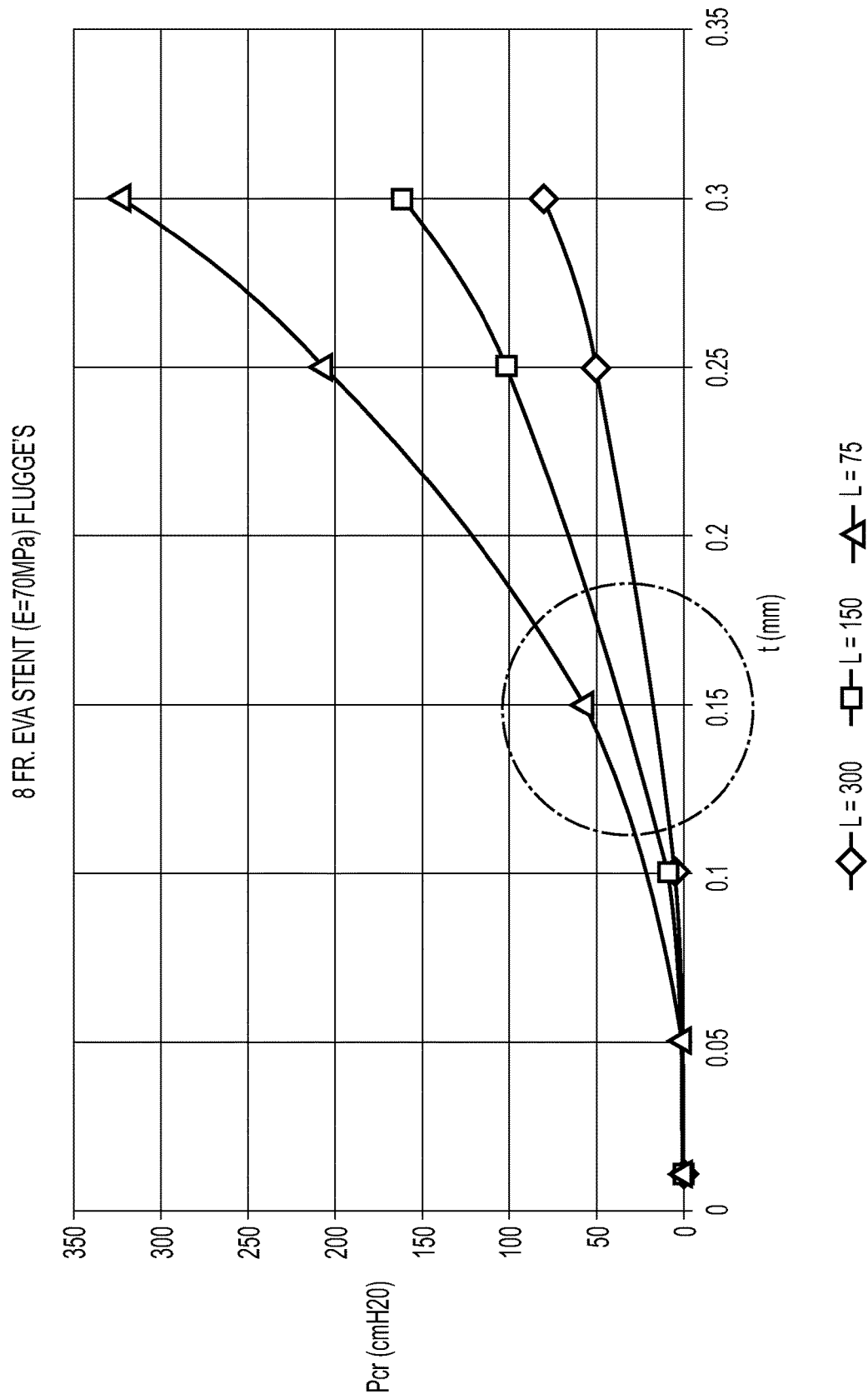

Referring specifically to FIG. 8, three different stents having a 8 Fr. size made of EVA material having a modulus of elasticity of 70 MPa were tested.

As illustrated in FIG. 8, a first stent having a second section with a length of 300 mm fell within the external pressure range of 40 cm H2O to 60 cm H2O at a wall thickness of about 0.23 mm to 0.25 mm. A second stent having a second section with a length of 150 mm fell within the pressure range of 40 cm H2O to 60 cm H2O at a wall thickness about 0.15 mm to 0.17 mm. A third stent having a second section with a length of 75 mm fell within the pressure range of 40 cm H2O to 60 cm H2O at a wall thickness about 0.12 mm to 0.15 mm.

Figure 9:
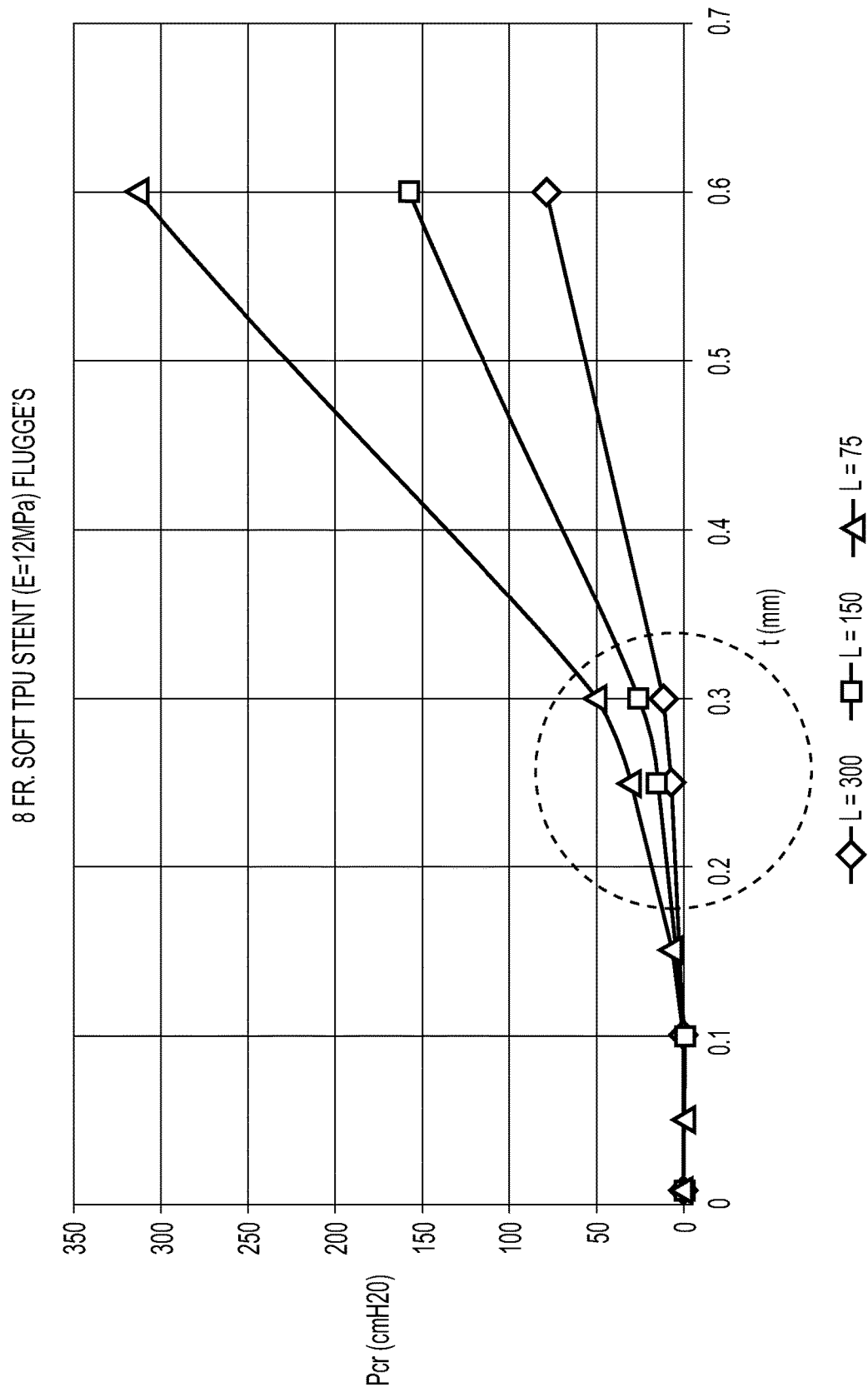

Referring specifically to FIG. 9, three different stents having a 8 Fr. size made of TPU material having a modulus of elasticity of 12 MPa were tested.

As illustrated in FIG. 9, a first stent having a second section with a length of 300 mm fell within the external pressure range of 40 cm H2O to 60 cm H2O at a wall thickness of about 0.4 mm to 0.5 mm. A second stent having a second section with a length of 150 mm fell within the pressure range of 40 cm H2O to 60 cm H2O at a wall thickness about 0.33 mm to 0.36 mm. A third stent having a second section with a length of 75 mm fell within the pressure range of 40 cm H2O to 60 cm H2O at a wall thickness about 0.25 mm to 0.3 mm.

Figure 10:
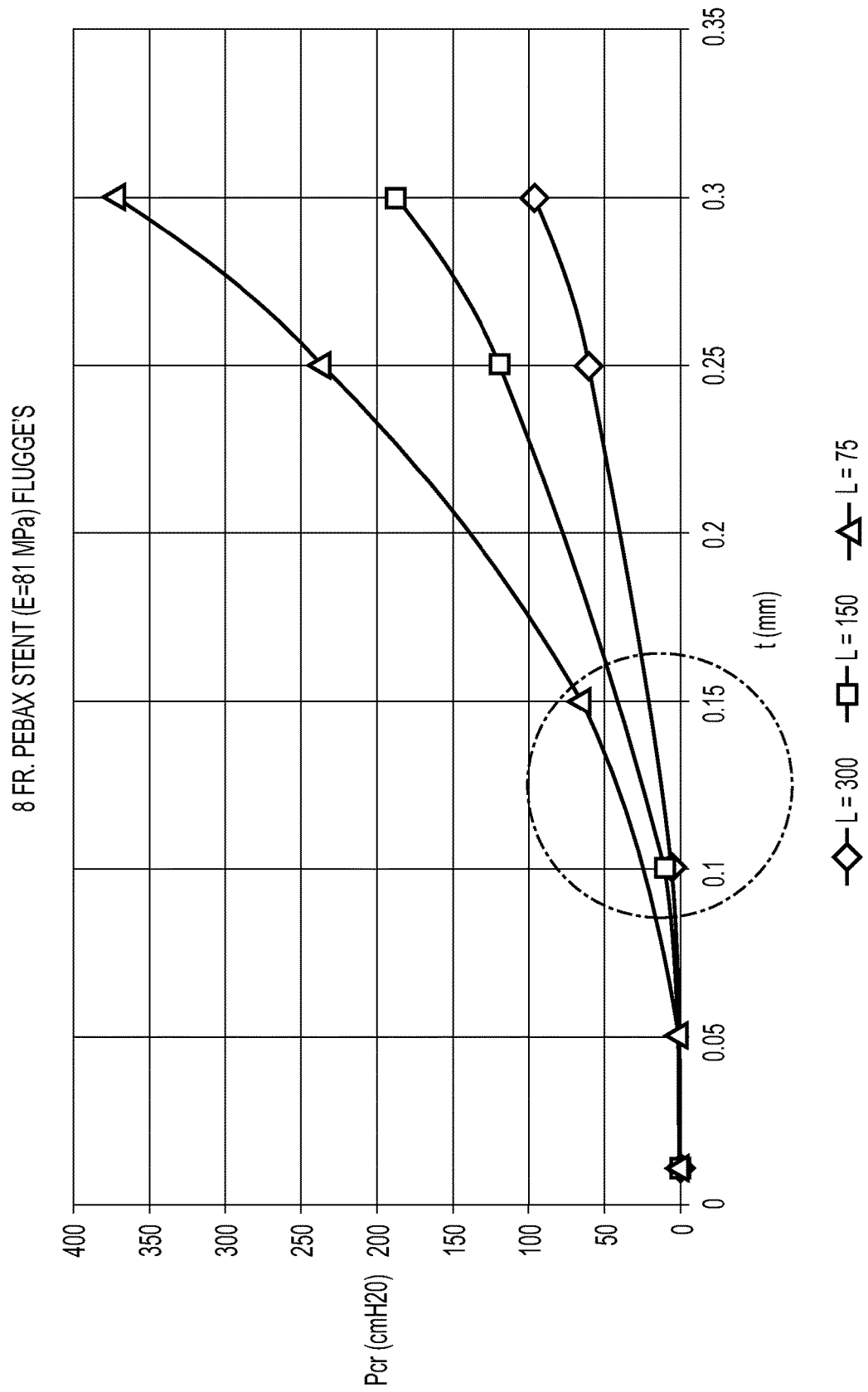

Referring specifically to FIG. 10, three different stents having a 8 Fr. size made of Pebax® material having a modulus of elasticity of 81 MPa were tested.

As illustrated in FIG. 10, a first stent having a second section with a length of 300 mm fell within the external pressure range of 40 cm H2O to 60 cm H2O at a wall thickness of about 0.18 mm to 0.25 mm. A second stent having a second section with a length of 150 mm fell within the pressure range of 40 cm H2O to 60 cm H2O at a wall thickness about 0.14 mm to 0.17 mm. A third stent having a second section with a length of 75 mm fell within the pressure range of 40 cm H2O to 60 cm H2O at a wall thickness about 0.13 mm to 0.15 mm.

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

By use of the term "may" herein, it is intended that any described attributes that "may" be included are optional.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A stent comprising:
   a first section having a first wall defining a first luminal section, the first wall having a first wall thickness and a first maximum diameter; and
   a second section, longitudinally separated from the first section, the second section having a second wall defining a second luminal section, the second luminal section having a second maximum diameter that is equal to the first maximum diameter and a plurality of walls defining luminal portions having a third maximum diameter less than the first maximum diameter, the second luminal section having a second wall thickness equal to the first wall thickness, the second luminal section enabled to close, along the luminal portions, at times external pressure is applied to the stent wherein the external pressure is 40 to 60 cm H2O.

2. The stent of claim 1, wherein the second wall has lower durometer than the first wall.

3. The stent of claim 1, wherein the first wall and the second wall are made of a polymer.

4. The stent of claim 1, wherein the second wall is made of chitosan.

5. The stent of claim 1, wherein the stent is a ureteral stent.

6. The stent of claim 5, wherein the second section is placed in a bladder of a patient.

7. The stent of claim 5, wherein the second section is placed in a ureter of a patient.

8. A stent, comprising:
   a first section having a first wall defining a first luminal section, the first section having a first maximum external diameter and a first wall thickness; and
   a second section, having a second wall defining a second luminal section, the second section having a second maximum external diameter that is equal to the first maximum external diameter and a minimum external diameter that is less than the first maximum external diameter, wherein the second luminal section has a second wall thickness equal to the first wall thickness, the second luminal section closes when an external pressure is applied to the stent, wherein the external pressure is 40 to 60 cm H2O.

9. The stent of claim 8, wherein the second section includes a plurality of walls defining luminal portions configured to close at times the external pressure is applied to the stent.

10. A stent comprising:
    a first section having a first wall defining a first luminal section, the first wall having a first wall thickness and a first maximum diameter; and
    a second section, longitudinally separated from the first section, the second section having a second wall defining a second luminal section, the second luminal section having a second maximum diameter that is equal to the first maximum diameter and a plurality of walls defining luminal portions having a third maximum diameter less than the first maximum diameter, the second luminal section having a second wall thickness equal to the first wall thickness, the second luminal section enabled to close, along the luminal portions, at times external pressure is applied to the stent, wherein the external pressure is 40 to 60 cm H2O.

11. The stent of claim 1, wherein the first section adjacent to the second section extends from the second section to an intermediate point, wherein a diameter of the first section from the intermediate point to the second section has a constant diameter.

* * * * *